(12) United States Patent  
Ting et al.

(10) Patent No.: US 9,833,527 B1  
(45) Date of Patent: Dec. 5, 2017

(54) ESCALATOR STERILIZATION DEVICE

(71) Applicant: LUNGHWA UNIVERSITY OF SCIENCE AND TECHNOLOGY, Taoyuan (TW)

(72) Inventors: Kuen Ting, Taoyuan (TW); Yi-Chuan Shih, Taoyuan (TW); Chih-Chien Hung, Taoyuan (TW); Hong-Ming Li, Taoyuan (TW); You-Hao Jin, Taoyuan (TW); Tien-Yu Wang, Taoyuan (TW); Jin Yih Kao, Taoyuan (TW)

(73) Assignee: LUNGHWA UNIVERSITY OF SCIENCE AND TECHNOLOGY, Taoyuan (TW)

( * ) Notice: Subject to any disclaimer, the term of this patent is extended or adjusted under 35 U.S.C. 154(b) by 0 days.

(21) Appl. No.: 15/383,722

(22) Filed: Dec. 19, 2016

(30) Foreign Application Priority Data

Oct. 24, 2016 (TW) .............................. 105134334 A

(51) Int. Cl.
*A61L 2/14* (2006.01)
*A61L 2/24* (2006.01)
*H05H 7/00* (2006.01)
*B66B 31/02* (2006.01)

(52) U.S. Cl.
CPC .................. *A61L 2/14* (2013.01); *A61L 2/24* (2013.01); *B66B 31/02* (2013.01); *H05H 7/001* (2013.01); *A61L 2202/11* (2013.01); *A61L 2202/14* (2013.01)

(58) Field of Classification Search
CPC ..... A61L 2/00; A61L 2/02; A61L 2/08; A61L 2/14; A61L 33/0094
USPC ........ 250/453.11, 454.11, 455.11; 422/1, 20, 422/21, 22, 23, 24
See application file for complete search history.

(56) References Cited

U.S. PATENT DOCUMENTS

| 2012/0241284 A1* | 9/2012 | Kobayashi | A61L 2/14 198/335 |
| 2012/0269677 A1* | 10/2012 | Zhou | A61L 9/22 422/4 |
| 2013/0064726 A1* | 3/2013 | Morfill | A01J 7/04 422/186.21 |

* cited by examiner

*Primary Examiner* — Nicole Ippolito
(74) *Attorney, Agent, or Firm* — Muncy, Geissler, Olds & Lowe, P.C.

(57) ABSTRACT

Disclosed is an escalator sterilization device attached close to a handrail of an escalator and formed by a base and a sterilization module. The sterilization module has a cover in an arc shape, so that the cover can be attached closed to a surface of a handrail of the escalator, and the inner wall of the cover has plural electrode coils electrically coupled to a power supply device in the base. After the power supply device is conducted by an electric power, a high voltage power is generated to excite the electrode coils to form plasma, and the plasma is used to destroy polymorphic bacteria and microorganisms, so that the sterilization module can eliminate the bacteria on the surface of the handrail of the escalator and provide a deodorant effect.

11 Claims, 11 Drawing Sheets

Reduction of bacteria after different time (0s, 1s, 5s, 3s, 6s, 9s, 12s, 15s) of plasma treatment (Escherichia coli).

ESCALATOR STERILIZATION DEVICE

BACKGROUND OF THE INVENTION

(a) Field of the Invention

The present invention relates to an escalator sterilization device, more particularly to the escalator sterilization device capable of eliminating bacteria attached on an escalator by low temperature plasma.

(b) Description of the Related Art

With reference to FIG. 1 for a conventional escalator 10, pedestrians stand on an automatic moving stair at an end of the escalator 10 and are moved to the other end of the escalator 10, wherein the stair is maintained at a level all the time while traveling, and a handrail 101 is installed separately on both sides of the escalator 10 and moved synchronously with the stair and provided for the pedestrians to hold. Although the escalator 10 of a public facility provides a convenient ride, the escalator 10 also becomes a means for spreading bacteria and viruses. Highly contagious viruses are popular, and pedestrians may be infected through their contact with public places, and the handrails 101 of the escalator 10 hide numerous invisible bacteria. Therefore, the handrails 101 of the escalator 10 are often sterilized manually from time to time. However, the manual intermittent sterilization not just fails to achieve a thorough disinfection and sterilization effect only, but also consumes much human resources. At present, there are no mandatory rules or regulations that require cleaning and sterilizing the handrails 101 of the escalator 10 everyday, and companies hesitate to clean and sterilize the handrails 101 of the escalator 10 periodically due to the consideration of the cost of the sterilization and cleaning. As a result, the handrails 101 of the escalator 10 usually contain a total number of bacteria exceeding a specified standard or close to a level of pollution. Since the escalator 10 is an item often in contact with people, a big loophole exists in the protection of public health. With reference to U.S. Pat. No. 9,034,270 B2 entitled "Plasma sterilization and cleaning treatment device for escalator, and escalator using the same", a plasma sterilization module installed inside the escalator has a planar discharge part capable of sterilizing a surface of a handrail of the escalator through ion emission (such as UV light) and provides a feasible solution of sterilizing the surface of the handrail of the escalator automatically and continuously. However, such device is installed inside the escalator and operated in a load-bearing status, and thus the power consumption is high. In addition, the escalators come with different internal structures, so that the installation of the escalators is very inconvenient, and the willingness of using such device is reduced.

SUMMARY OF THE INVENTION

Therefore, it is a primary objective of the present invention to provide a convenient escalator sterilization device capable of sterilizing and disinfecting the handrails of the escalator continuously and automatically, even when the escalator is not in a load-bearing status.

According to the invention, an escalator sterilization device attached includes a base and a sterilization module. The sterilization module has a cover in an arc shape, so that the cover can be attached closed to a surface of a handrail of the escalator, and the inner wall of the cover has plural electrode coils electrically coupled to a power supply device in the base. After the power supply device is conducted by an electric power, a high voltage power is generated to excite the electrode coils to form plasma, and the plasma is used to destroy polymorphic bacteria and microorganisms, so that the sterilization module can eliminate the bacteria on the surface of the handrail of the escalator and provide a deodorant effect.

DETAILED DESCRIPTION OF THE PREFERRED EMBODIMENT

The technical measures and characteristics of the present invention will become apparent with the detailed description of preferred embodiments accompanied with related drawings as follows. It is noteworthy that the preferred embodiments and drawings are provided for the purpose of illustrating the present invention, but not intended for limiting the scope of the invention. Therefore, the drawings are not necessarily drawn in the actual scale or proportion. In addition, same numerals are used for representing the same respective elements.

Figure 1:
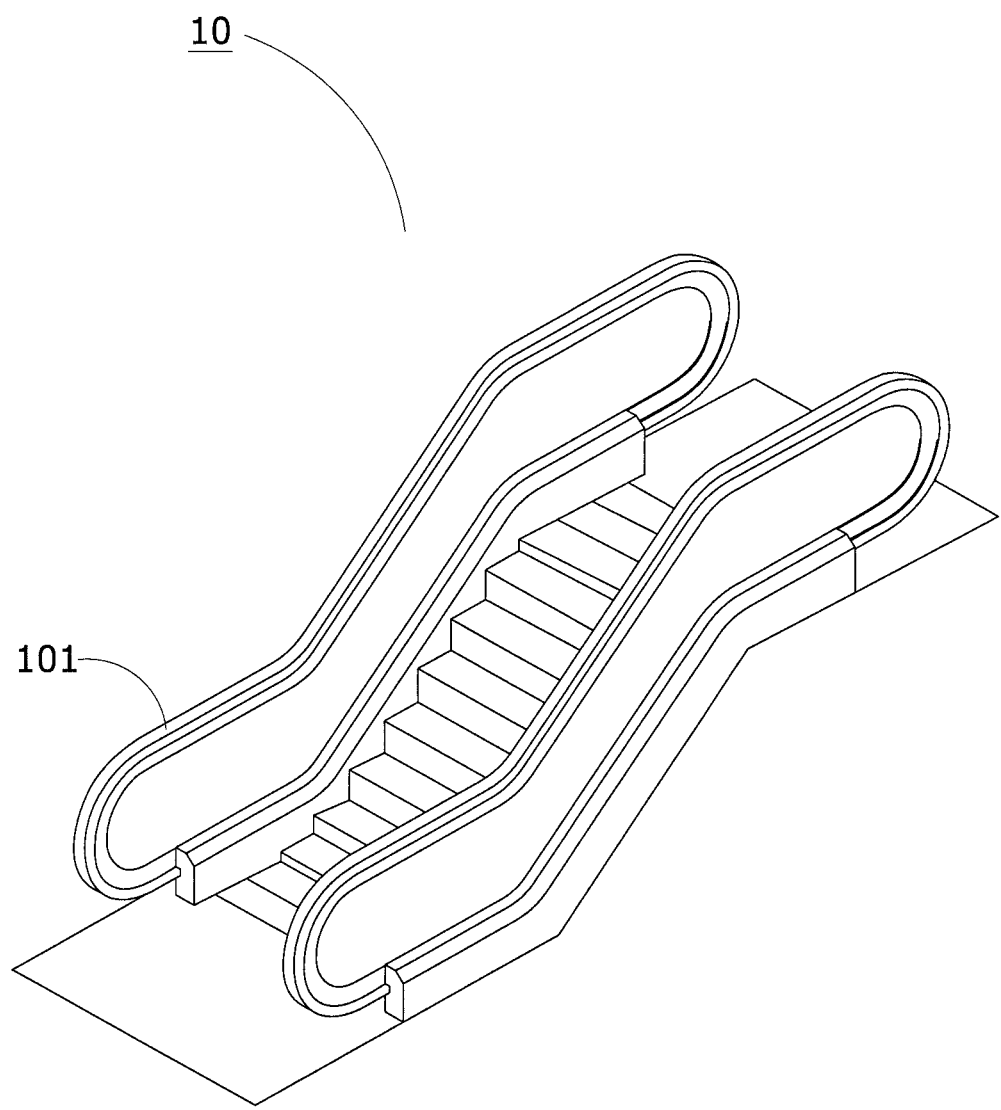
FIG. 1 is a perspective view of a conventional escalator.
Figure 2:
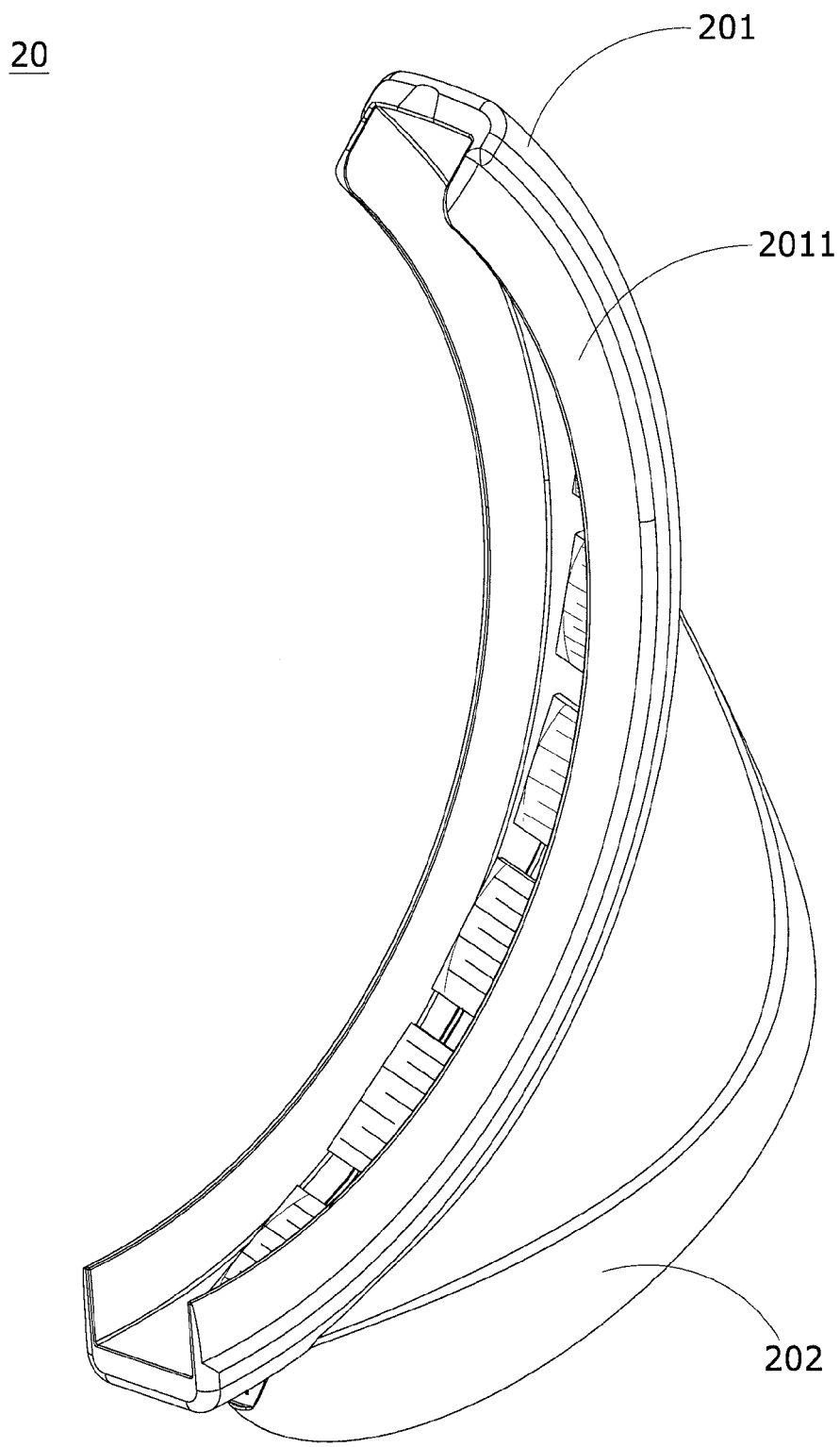
FIG. 2 is a perspective view of the present invention.

With reference to FIG. 2 for an escalator sterilization device 20 of the present invention, the escalator sterilization device 20 comprises a sterilization module 201 and a base 202, wherein the sterilization module 201 has a cover 2011 in an arc shape and attachable on a surface of a handrail 101 of an escalator 10, and the cover 2011 is installed to a base 202 and normally perpendicular to the cover 2011.

Figure 3:
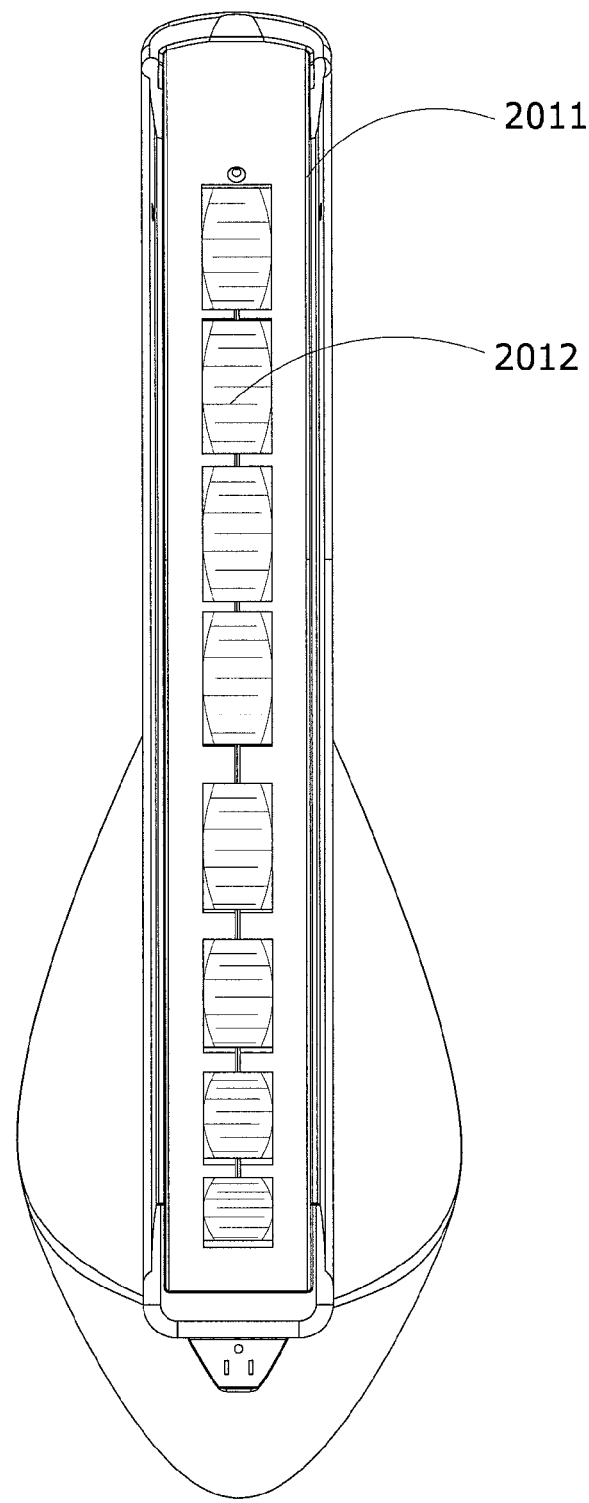
FIG. 3 is a schematic view of a sterilization module of the present invention.

With reference to FIG. 3, the cover 2011 has a plurality of electrode coils 2012 disposed on an inner wall of the cover 2011, preferably distributed all over the cover 2011, and the electrode coils 2012 are arranged in a spiral shape, an S-shape, a cross shape, or a curved-edge capacitive way. The electrode coils 2012 of the present invention are primarily arranged in the curve-edge capacitive way, but the invention is not limited to such arrangement only.

Figure 4:
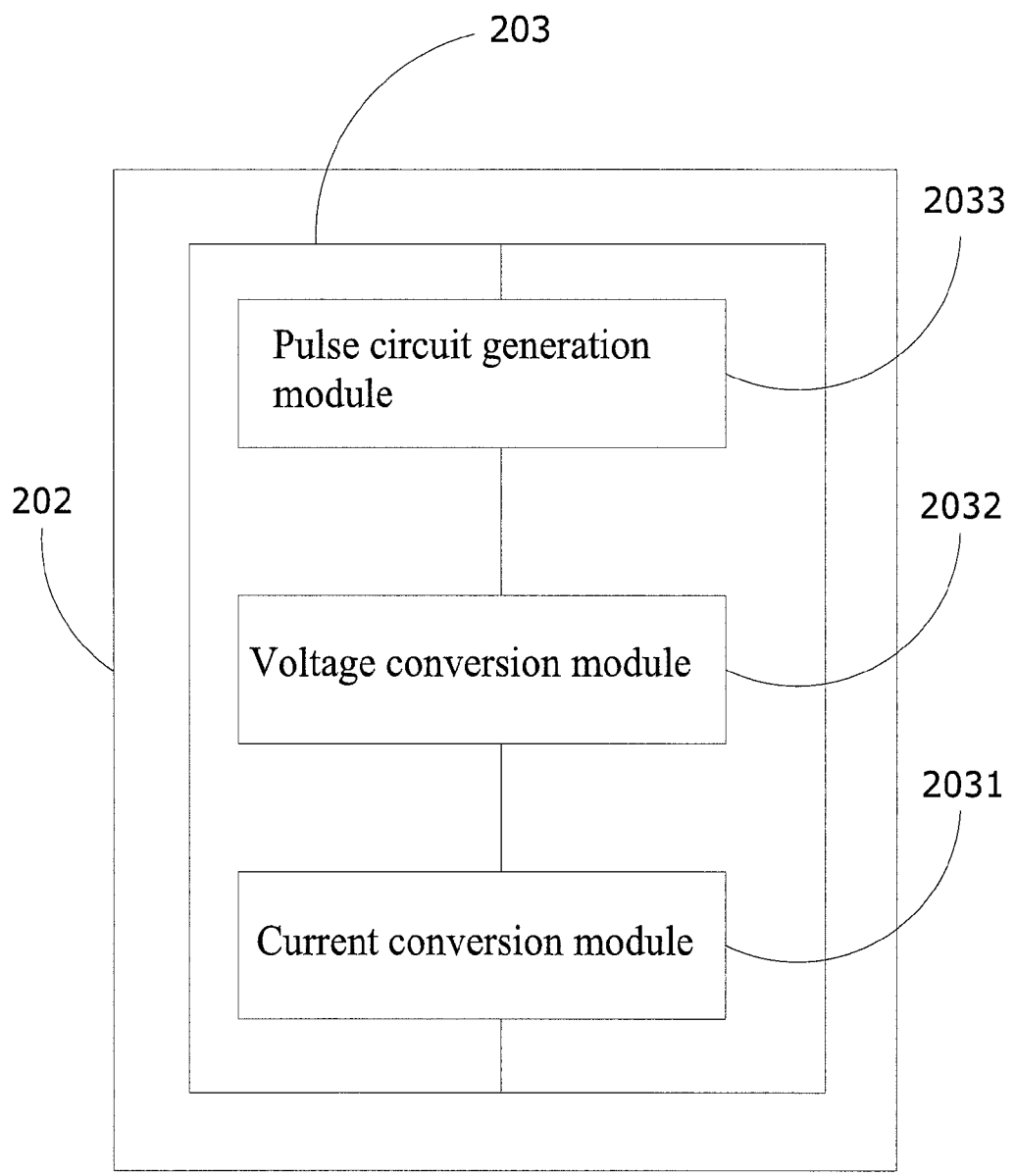
FIG. 4 is a block diagram of a base of the present invention.

With reference to FIGS. 3 and 4, the base 202 has a power supply device 203 installed therein, and the power supply device 203 has a current conversion module 2031, a voltage conversion module 2032 and a pulse circuit generation module 2033, wherein the current conversion module 2031 is for converting alternating current (AC) into direct current (DC), and the voltage conversion module 2032 is for converting a low voltage into a high voltage, and the pulse circuit generation module 2033 is for generating a pulse voltage, and the power supply device 203 is electrically coupled to the plurality of electrode coils 2012. After the power supply device 203 is electrically conducted by an external power, the electrode coils 2012 are excited to form plasma.

Figure 5:
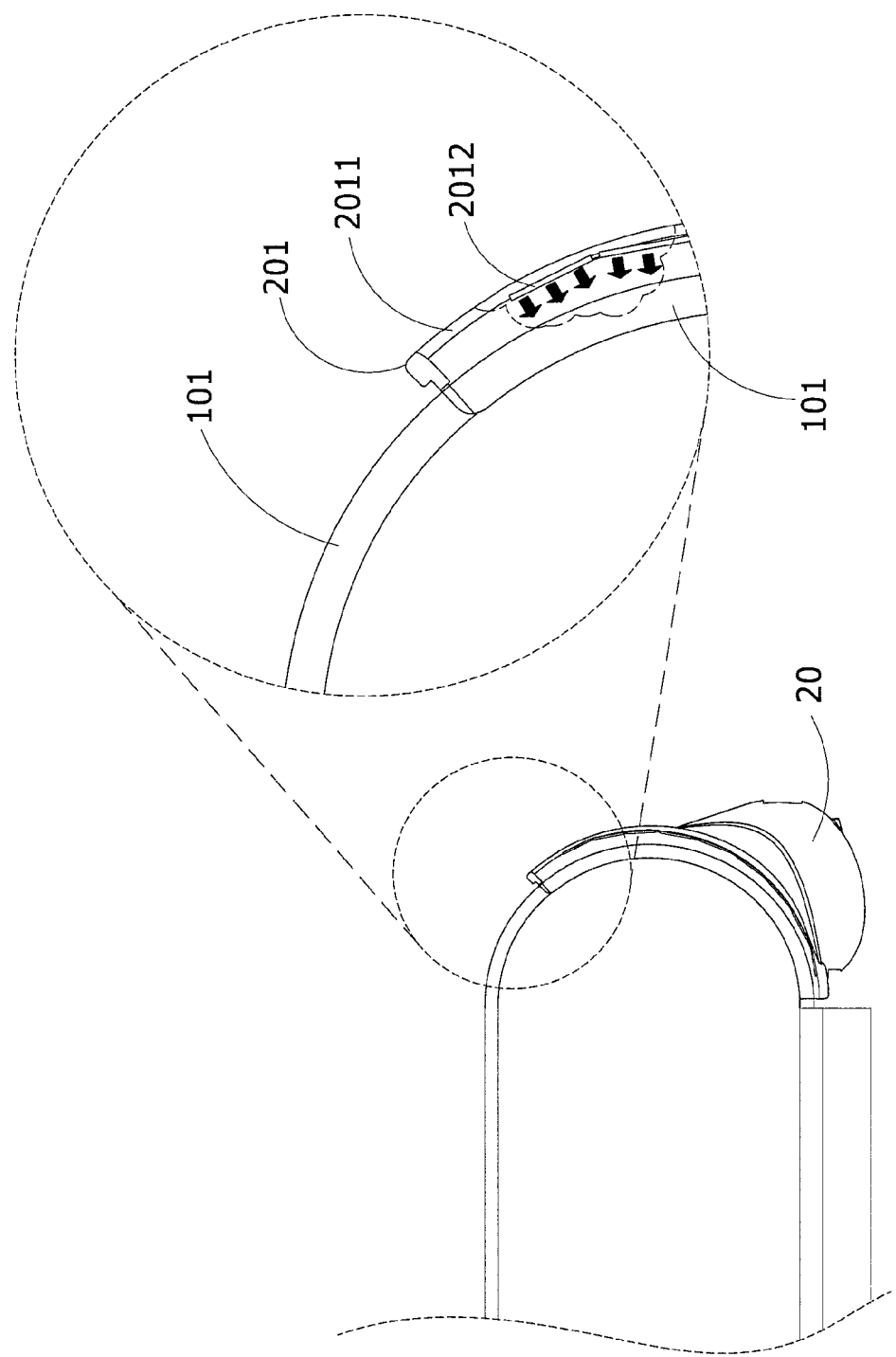
FIG. 5 is a schematic view of a first embodiment of the present invention.

With reference to FIG. 5 for an embodiment of the present invention, the cover 2011 of the sterilization module 201 is attached to the surface of the handrail 101 of the escalator 10. After the power supply device 203 is electrically conducted by an external power, the current conversion module 2031 converts the alternating current into the direct current, and the pulse circuit generation module 2033 generates an instant high voltage to excite the electrode coils 2012 to form plasma, and the plasma is irradiated onto the surface of the handrail 101, so that the plasma will destroy polymorphic bacteria and microorganisms attached on the surface of the handrail 101. The handrail 101 of the escalator 10 is turned cyclically to be disinfected by the sterilization module 201 so as to achieve a continuous and automatic sterilization effect, and the electrode coils 2012 are operated normally even when the escalator is not situated in the load-bearing status.

Figure 6:
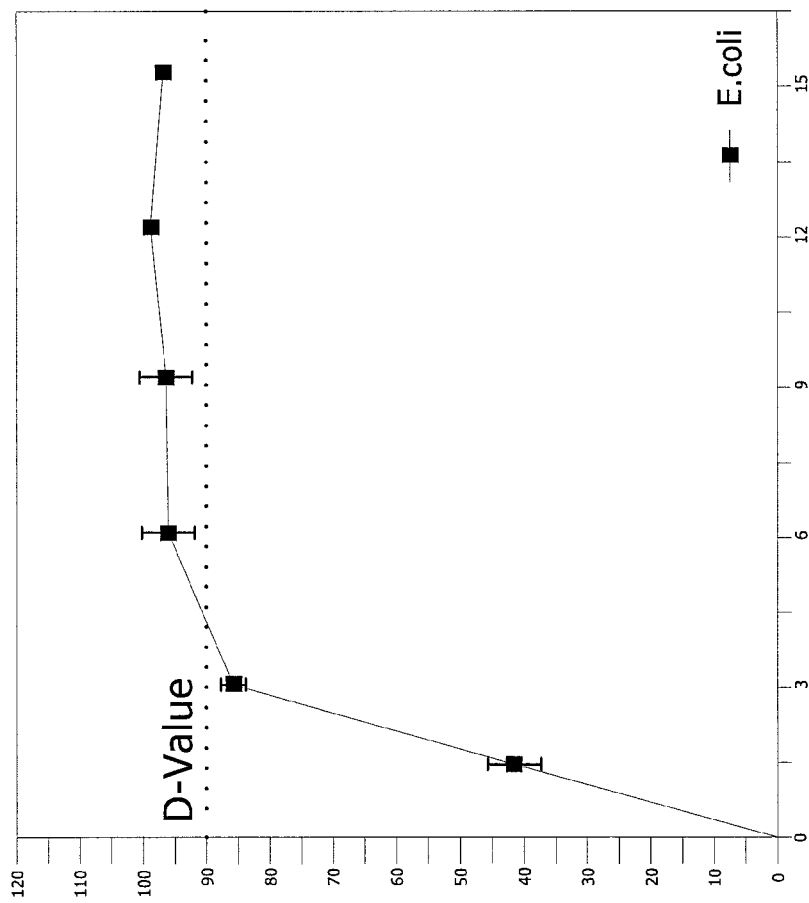
FIG. 6 is a first graph showing the experiment data of the sterilization effect.

With reference to FIG. 6 for a graph showing the actual experiment data of the sterilization effect when a plasma reactor with curved-edge capacitive electrode coils is used for the experiment, the initial bacterial concentration of *Escherichia coli* (*E-coli*) is $10^7$ CFU/ml (CFU, a colony-forming unit being a unit used to estimate the number of viable bacteria or fungal cells in a sample), and when the power supply device 203 supplies an AC power and the power frequency of which is 5.208 kHz and the power is 0.489 W, the result as shown in the figure will be achieved after the sterilization process is carried out by the plasma with such intensity for 0 to 15 seconds. The D-value (D-value referring to decimal reduction time and is the time required at a given condition, or set of conditions, to kill 90% of the exposed microorganisms) will be reached after 4 seconds of the processing, and all bacteria are eliminated after 12 seconds of processing.

Figure 7:
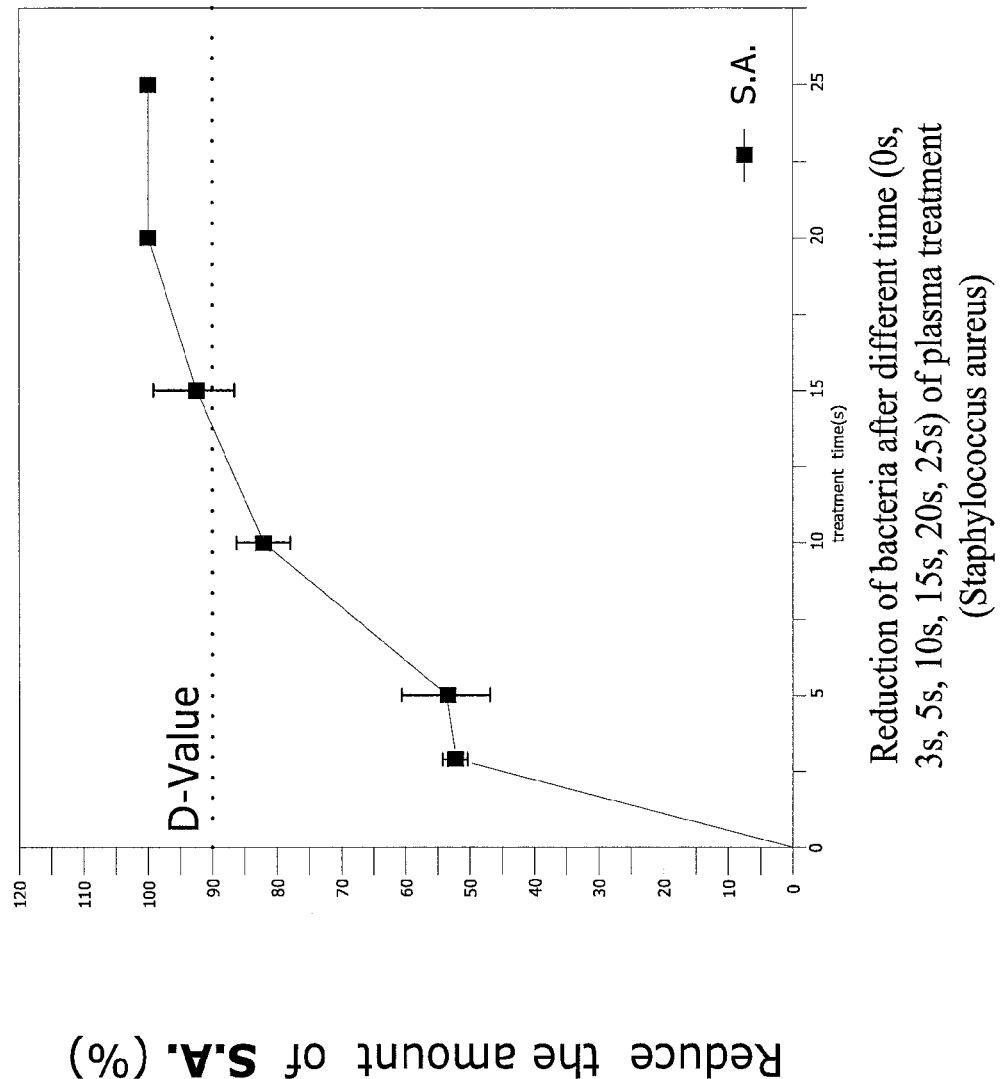
FIG. 7 is a second graph showing the experiment data of the sterilization effect.

With reference to FIG. 7 for a graph showing the actual experiment data of the sterilization effect when a plasma reactor with curved-edge capacitive electrode coils is used for the experiment, the initial bacterial concentration of *Staphylococcus aureus* (*S. aureus*) is $10^7$ CFU/ml, and when the power supply device 203 supplies an AC power and the power frequency of which is 5.208 kHz and the power is 0.489 W, the result as shown in the figure will be achieved after the sterilization process is carried out by the plasma with such intensity for 0 to 25 seconds. The value of D will be reached after 15 seconds of processing, and all bacteria are eliminated after 20 seconds of processing. The experiment results show that the present invention has a significant sterilization effect. The longer the processing time, the better the sterilization effect.

Figure 8:
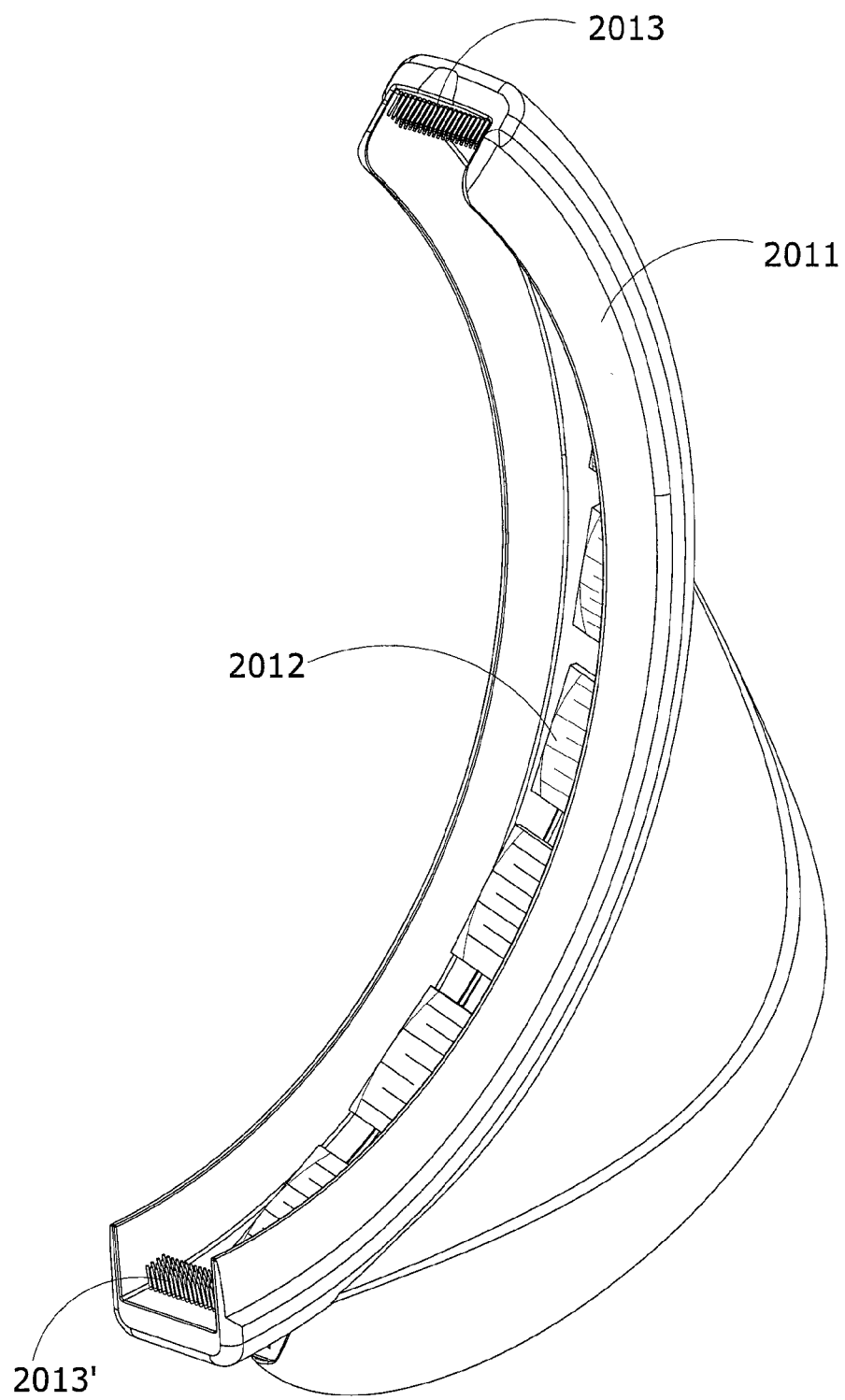
FIG. 8 is a schematic view of a second embodiment of the present invention.

With reference to FIG. 8, both ends of the cover 2011 have a cleaning portion (2013, 2013') to improve the sterilization effect, wherein the cleaning portion (2013, 2013') may be a brush. When the handrail 101 of the escalator 10 is operated to pass the cleaning portion 2013 of the cover 2011, the more conspicuous dirt attached on the surface of the handrail 101 is wiped and cleaned by the cleaning portion (2013, 2013'), and the plasma produced by the electrode coils 2012 further sterilizes the surface of the handrail 101, so as to provide a double-sterilization effect.

Figure 9:
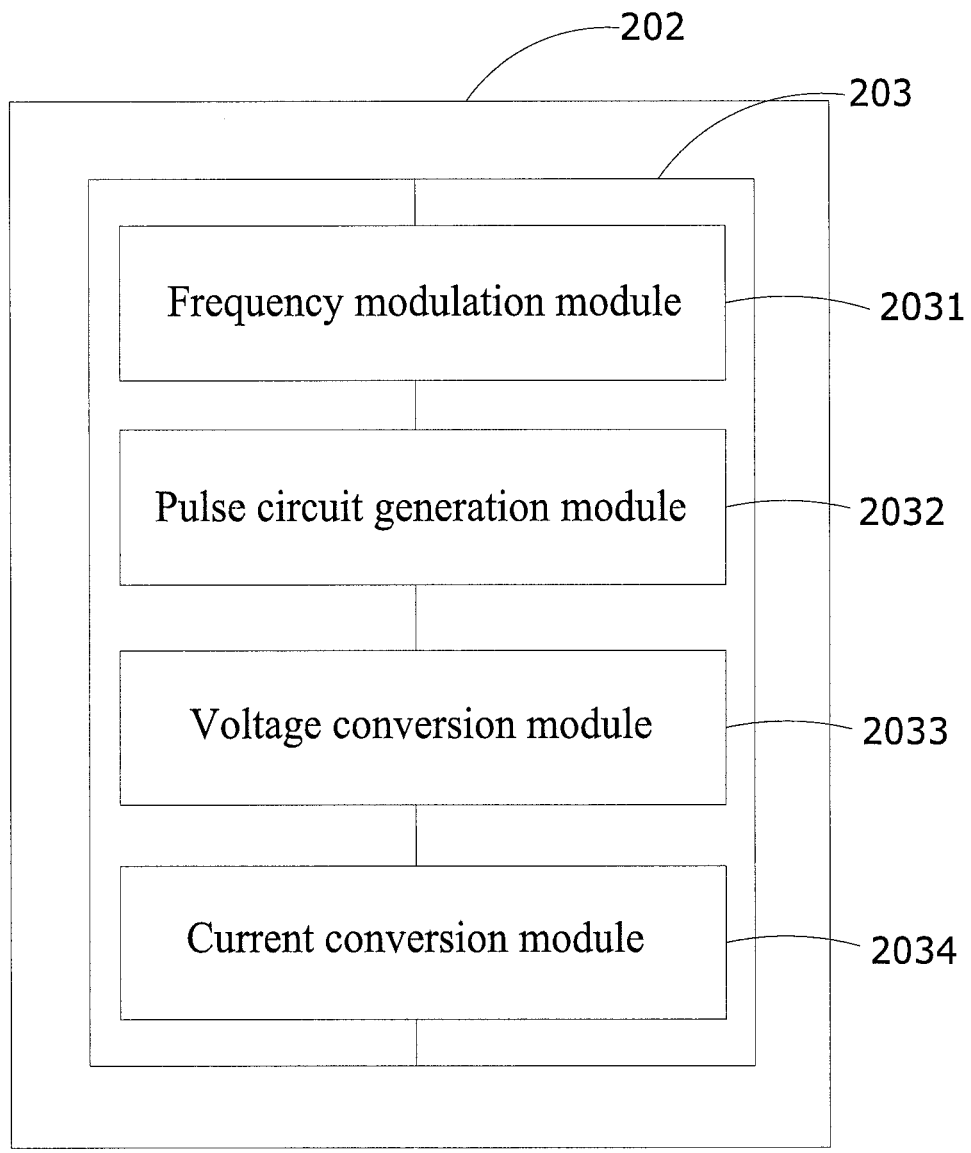
FIG. 9 is a block diagram of a third embodiment of the present invention.

With reference to FIG. 9, the power supply device 203 further comprises a frequency modulation module 2034 for adjusting a frequency of the plasma. After the power supply device 203 is electrically conducted by an external power, the frequency modulation module 2034 will adjust the frequency of the plasma to increase the intensity of the plasma for a better sterilization effect.

Figure 10:
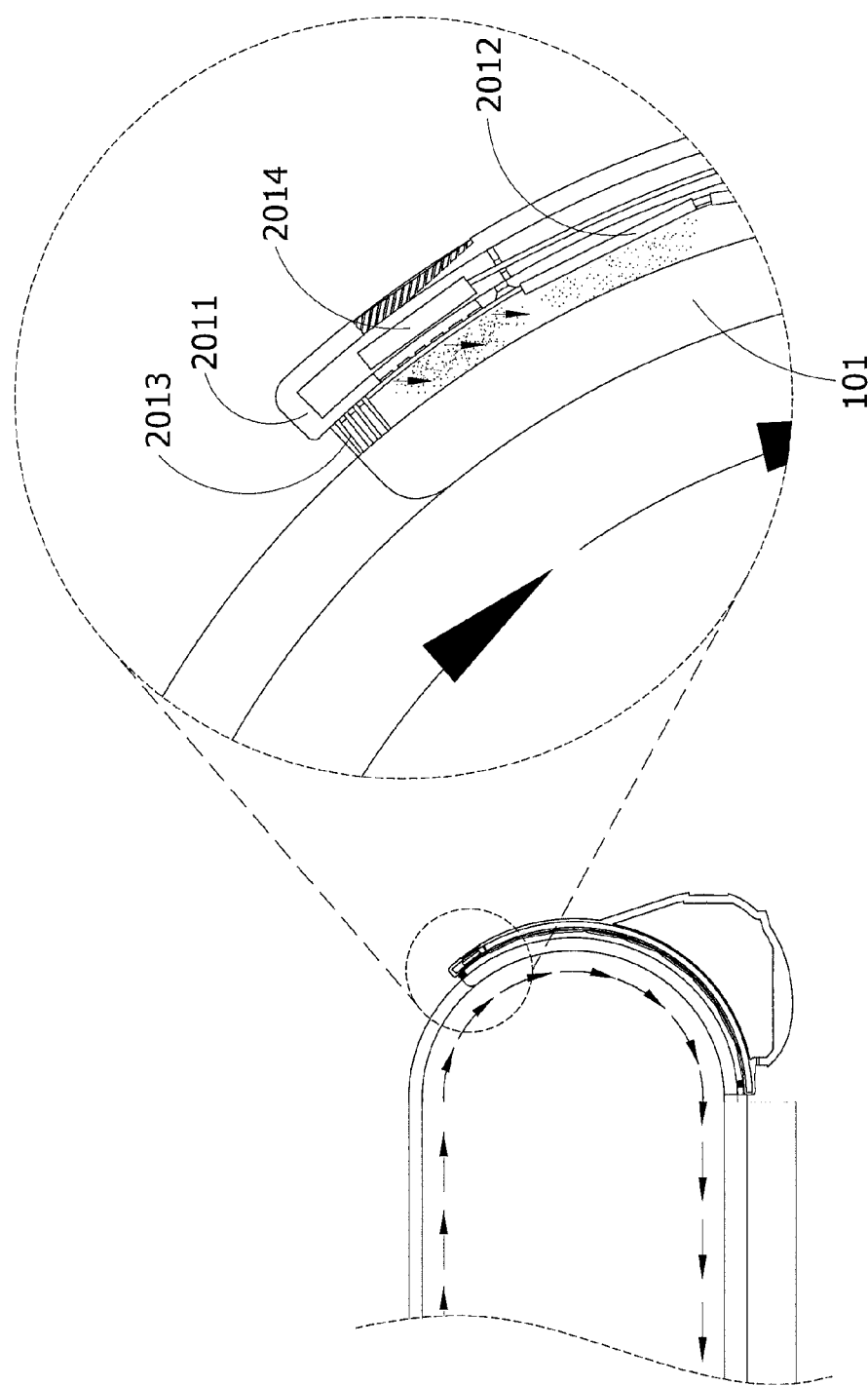
FIG. 10 is a schematic view of a fourth embodiment of the present invention.

With reference to FIG. 10, microparticles are produced after the plasma is produced by the electrode coils 2012, and the microparticles may be inhaled by respiratory tract of human to jeopardize human health. To prevent the microparticles from floating into the air, a fan module 2014 is installed at an upper end of the cover 2011 and at a position proximate to the cleaning portion 2013, so that the microparticles formed after the plasma is produced by the electrode coils 2012 will be blown away by the wind of the fan module 2014, and the microparticles will flow downwardly from the cover 2011 and concentrate at a position below the cover 2011, so as to prevent the microparticles from floating upwardly or being inhaled by human bodies.

Figure 11:
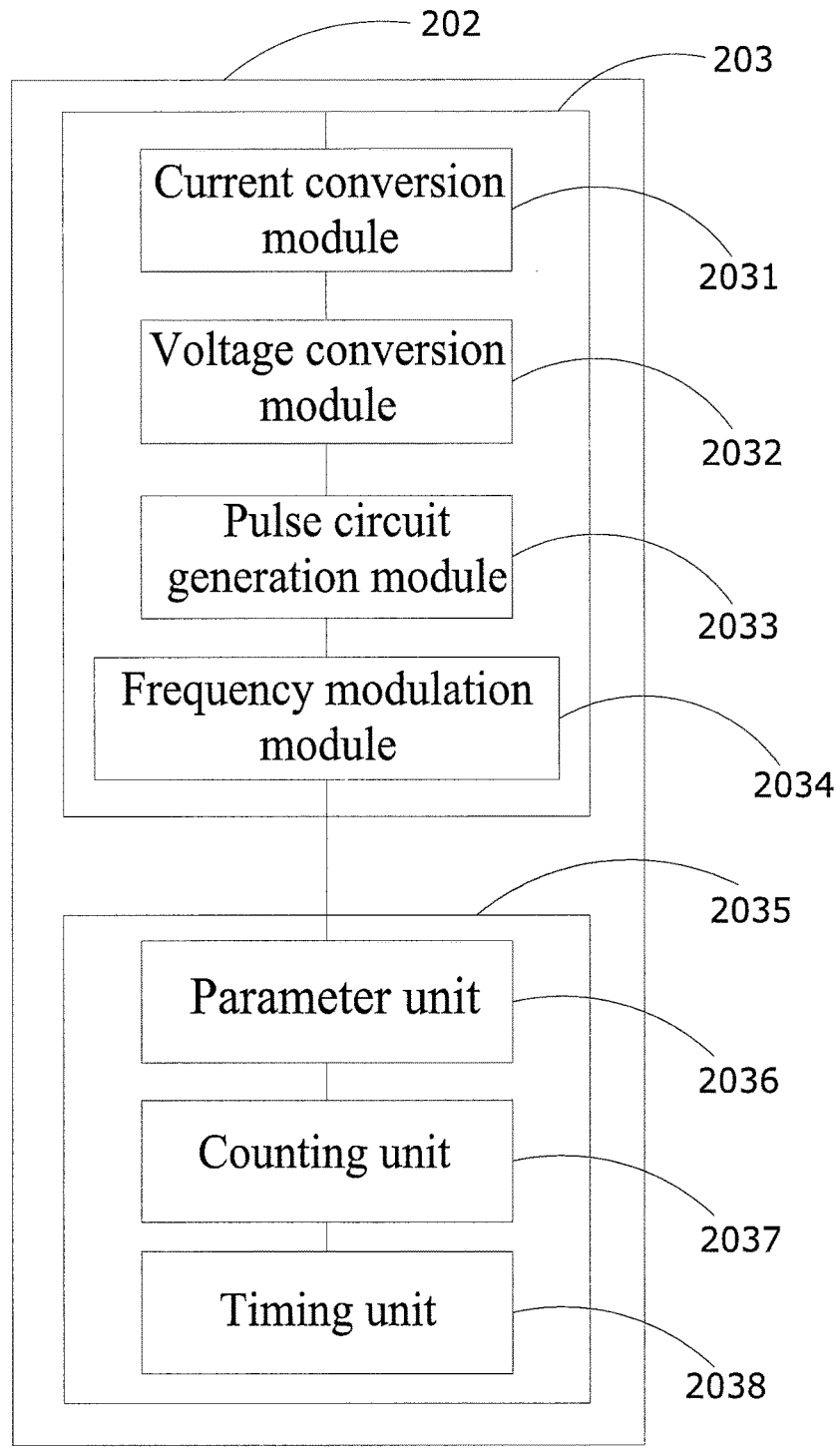
FIG. 11 is a block diagram of a fifth embodiment of the present invention.

With reference to FIG. 11, the base 202 has a sensing module 2035 electrically coupled to the frequency modulation module 2034, and the sensing module 2035 has a parameter unit 2036, a counting unit 2037 and a timing unit 2038, wherein the parameter unit 2036 pre-stores a reference value of a downgraded frequency of plasma. For example, when the detected number of people reaches a predetermined number, the frequency of plasma will be incremented (such as 50, 100, 150, etc). After a certain period of time (such as 30 minutes, 1 hour, etc), the frequency of plasma will be decremented to a relevant reference value if the number of people no longer increases. The counting unit 2037 is provided for detecting and calculating the number of people passing through the escalator, and the timing unit 2038 is provided for calculating the number of people which does not increase further. In addition, the sensing module 2035 may be used to calculate the number of people who pass through the escalator 10, and if the number of people passing through the escalator 10 increases, then the sensing module 2035 will drive the frequency modulation module 2034 to increase the frequency of plasma, and the counting unit 2037 counts the number of people passing through the escalator 10 to determine whether or not to increment the frequency of plasma, and the timing unit 2038 is used to determine whether or not to decrement the frequency of plasma, and the sensing module 2035 can improve the sterilization effect of the present invention and achieve the power and energy saving effect. In addition, the sensing module 2035 may be installed at an entrance or exit of a public place such as the entrance or exit of a department store and then electrically coupled to the frequency modulation module 2034 of the power supply device 203 of the present invention. However, the invention is not just limited to such arrangement only.

As described above, the present invention adopts a cover substantially in an arc shape, so that the cover can be attached closely to the surface of the handrail of the escalator without requiring a complicated installation operation. After the power supply device is electrically conducted by an external power, the electrode coils are excited to form plasma which is irradiated onto the handrail surface continuously to achieve the disinfection and sterilization effects. With the aforementioned implementation, the present invention provides a convenient escalator sterilization device capable of automatically and continuously sterilizing the handrails of the escalator even not in a load bearing status.

Many changes and modifications in the above-described embodiments of the invention can, of course, be carried out without departing from the scope thereof. Accordingly, to promote the progress in science and the useful arts, the invention is disclosed and is intended to be limited only by the scope of the appended claims.

What is claimed is:

1. An escalator sterilization device, attached closely on a surface of a handrail of an escalator, comprising:
   a sterilization module, having an cover in an arc-shape, and a plurality of electrode coils disposed on an inner wall of the cover; and
   a base, for installing the cover thereon, and having a power supply device installed therein and electrically coupled to the plurality of electrode coils;
   thereby, after the power supply device is electrically conducted by an external power, the plurality of electrode coils are excited to form plasma, and the plasma is provided for sterilizing the surface of the handrail.

2. The escalator sterilization device of claim 1, wherein the power supply device comprises a current conversion module, a voltage conversion module and a pulse circuit generation module, and the current conversion module is for converting an alternate current into a direct current, and the voltage conversion module is for converting a low voltage into a high voltage, and the pulse circuit generation module is for generating a pulse voltage.

3. The escalator sterilization device of claim 2, wherein the power supply device comprises a frequency modulation module for modulating a frequency to improve intensity of plasma excitation.

4. The escalator sterilization device of claim 3, wherein the base has a sensing module electrically coupled to the frequency modulation module of the power supply device.

5. The escalator sterilization device of claim 4, wherein the sensing module has a parameter unit, a counting unit, and a timing unit.

6. The escalator sterilization device of claim 3, wherein the frequency modulation module and the sensing module are electrically coupled.

7. The escalator sterilization device of claim 6, wherein the sensing module has a parameter unit, a counting unit, and a timing unit.

8. The escalator sterilization device of claim 1, wherein the electrode coils are arranged in a regular manner.

9. The escalator sterilization device of claim 8, wherein the electrode coils are arranged in a curved-edge capacitive way.

10. The escalator sterilization device of claim 1, wherein both ends of the cover respectively have a cleaning portion.

11. The escalator sterilization device of claim 10, wherein a fan module is installed at an upper end of the cover and at a position proximate to the cleaning portion.

* * * * *